United States Patent
Masui et al.

(10) Patent No.: US 8,115,030 B2
(45) Date of Patent: Feb. 14, 2012

(54) PROCESS FOR THE PREPARATION OF SULFOMATE-CARBOXYLATE DERIVATIVES

(75) Inventors: Toshiaki Masui, Hyogo (JP); Kazuhiro Yoshida, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 1084 days.

(21) Appl. No.: 11/909,980

(22) PCT Filed: Mar. 30, 2006

(86) PCT No.: PCT/JP2006/306616
§ 371 (c)(1), (2), (4) Date: Sep. 27, 2007

(87) PCT Pub. No.: WO2006/106800
PCT Pub. Date: Oct. 12, 2006

(65) Prior Publication Data
US 2008/0262264 A1    Oct. 23, 2008

(30) Foreign Application Priority Data
Mar. 31, 2005 (JP) .................. 2005-102678

(51) Int. Cl.
C07C 303/00    (2006.01)
(52) U.S. Cl. .......................... 564/98; 560/125
(58) Field of Classification Search .................. None
See application file for complete search history.

(56) References Cited

FOREIGN PATENT DOCUMENTS

| EP | 1249233 A1 | 10/2002 |
| EP | 1484301 | * 8/2004 |
| EP | 1484301 A1 | 12/2004 |
| WO | WO-0137826 A1 | 5/2001 |
| WO | WO-03/076374 A1 | 9/2003 |
| WO | WO 03076374 | * 9/2003 |

* cited by examiner

*Primary Examiner* — Andrew D Kosar
*Assistant Examiner* — Yate K Cutliff
(74) *Attorney, Agent, or Firm* — Birch, Stewart, Kolasch & Birch, LLP

(57) ABSTRACT

Disclosed is a process for the preparation of Compound (III), salt or solvate thereof by reacting Compound (I), salt or solvate thereof with Compound (II) in a toluene solvent in the presence of an additive such as water or an alcohol. Also disclosed is a process for the preparation of Compound (IV) comprising hydrolyzing the obtained Compound (III) if necessary, and then oxidizing.

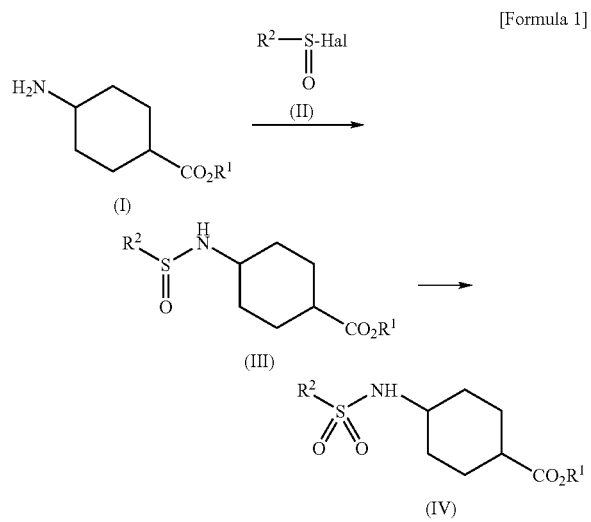

In the formula, $R^1$ is hydrogen, optionally substituted lower alkyl, optionally substituted aryl or optionally substituted aryl lower alkyl, and $R^2$ is optionally substituted lower alkyl, optionally substituted cycloalkyl or optionally substituted aryl lower alkyl.

5 Claims, No Drawings

PROCESS FOR THE PREPARATION OF SULFOMATE-CARBOXYLATE DERIVATIVES

This application is a 371 PCT National Phase of International Application No. PCT/JP2006/306616, filed Mar. 30, 2006 which claims priority of JP 2005-102678, filed Mar. 31, 2005, both of which are incorporated by reference herein.

TECHNICAL FIELD

The present invention relates to a process for the preparation of sulfamate-carboxylate derivatives.

BACKGROUND ART

Sulfamate-carboxylate derivatives are useful compounds as synthetic materials or intermediates for medicine. For example, they can be used as a synthetic intermediate of a compound having NPYY5 receptor antagonistic activity described in Patent Document 1.

Patent Document 1 discloses a process for the preparation of 4-(2-methylpropane-2-sulfonylamino-1-cyclohexanecarboxylic acid comprising subjecting 4-amino-1-cyclohexanecarboxylic acid methyl ester and t-butylsulphinyl chloride to the coupling reaction in a dichloromethane solvent, oxidizing the obtained compound, and then hydrolyzing. It is difficult to use industrially this process, because it is necessary that restricted-use dichloromethane is used and the product is isolated by chromatography.

Patent Document 2 discloses a process for the preparation of trans-4-(2-methylpropane-2-sulfonylamino-1-cyclohexanecarboxylic acid comprising subjecting cis-4-amino-1-cyclohexanecarboxylic acid methyl ester and t-butylsulphinyl chloride to the coupling reaction in an ethyl acetate solvent, the oxidation reaction, transformation to trans isomer, and then hydrolysis. This process was far from a high-yielding preparation process as the yield from cis-4-amino-1-cyclohexanecarboxylic acid to trans-4-(2-methylpropane-2-sulfonylamino)cyclohexanecarboxylic acid is 70% or less even if the loss in transformation to trans isomer was excluded.

Additionally, the document discloses an example that tetrahydrofuran is used in a coupling step. However, the process was needed to improve as a process for the industrial preparation, because it was necessary to isolate the reaction intermediates in every step, operations were complicated and the preparation efficiency was not high.

[Patent Document 1] WO01/37826
[Patent Document 2] WO2003/076374

DISCLOSURE OF INVENTION

Problems to be Solved by the Invention

The object of the present invention is to provide an efficient process for the preparation of sulfamate-carboxylate derivatives which are useful as synthetic materials or intermediates for medicine.

Means for Solving the Problem

The present invention is the followings.
(1) A process for the preparation of a compound of the formula (III):

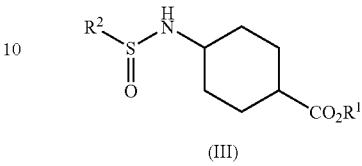

[Formula 3]

(III)

wherein $R^1$ is hydrogen, optionally substituted lower alkyl, optionally substituted aryl or optionally substituted aryl lower alkyl, and $R^2$ is optionally substituted lower alkyl, optionally substituted cycloalkyl or optionally substituted aryl,
salt or solvate thereof (hereinafter referred to as Compound (III)),
characterized by reacting a compound of the formula (I):

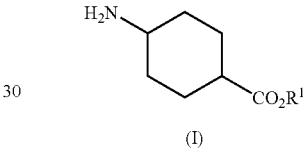

[Formula 1]

(I)

wherein $R^1$ has the same meaning as defined above,
salt or solvate thereof (hereinafter referred to as Compound (I)),
with a compound of the formula (II):

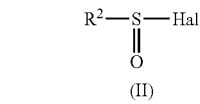

[Formula 2]

(II)

wherein $R^2$ has the same meaning as defined above, and Hal is halogen (hereinafter referred to as Compound (II)),
in toluene solvent in the presence of at least one of additives selected from the group consisting of water, alcohol, dimethylformamide, dimethylacetamide and dimethoxyethane.
(2) The process for the preparation of the above (1), wherein the additive is water or isopropanol.
(3) A process for the preparation of a compound of the formula (IV):

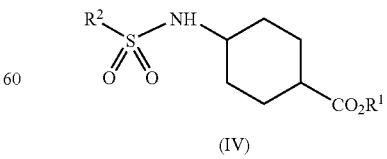

[Formula 4]

(IV)

wherein $R^1$ and $R^2$ have the same meanings as defined above,
salt or solvate thereof (hereinafter referred to as Compound (IV)), characterized by obtaining a compound of the formula (III), salt or solvate thereof by the process of the above (1), and oxidizing the obtained compound, salt or solvate thereof.
(4) A process for the preparation of a compound of the formula (IVb):

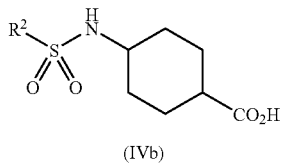

[Formula 7]

(IVb)

wherein $R^2$ has the same meaning as defined above,
salt or solvate thereof (hereinafter referred to as Compound (IVb)),
characterized by hydrolyzing a compound of the formula (IIIa):

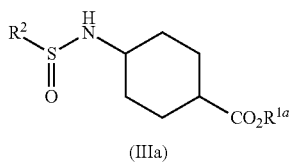

[Formula 5]

(IIIa)

wherein $R^{1a}$ is optionally substituted lower alkyl, optionally substituted aryl or optionally substituted aryl lower alkyl, and $R^2$ has the same meaning as defined above,
salt or solvate thereof (hereinafter referred to as Compound (IIIa)),
to obtain a compound of the formula (IIIb):

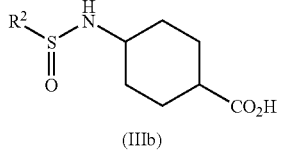

[Formula 6]

(IIIb)

wherein $R^2$ has the same meaning as defined above,
salt or solvate thereof (hereinafter referred to as Compound (IIIb)),
and oxidizing the obtained compound, salt or solvate thereof.
(5) The process for the preparation of the above (4), characterized by obtaining a compound of the formula (IIIa):

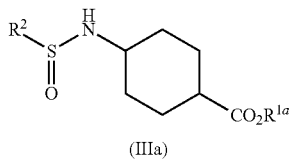

[Formula 8]

(IIIa)

wherein $R^{1a}$ and $R^2$ have the same meanings as defined above,
salt or solvate thereof by the process of the above (1), and using the obtained compound, salt or solvate thereof.
(6) The process for the preparation of the above (5), characterized by reacting without isolating a compound of the formula (IIIa) or (IIIb) or the salt to give a compound of the formula (IVb), salt or solvate thereof.
(7) A process for the preparation of a compound of the formula (VI):

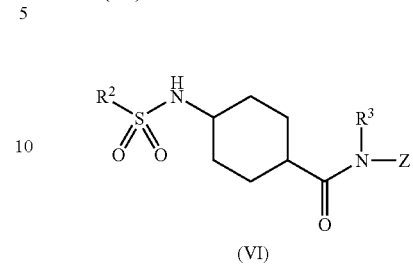

[Formula 9]

(VI)

wherein $R^2$, $R^3$ and Z have the same meanings as defined above,
pharmaceutically acceptable salt or solvate thereof (hereinafter referred to as Compound (VI)),
characterized by obtaining a compound of the formula (IV) or (IVb), salt or solvate thereof by the process of any one of the above (3) to (6), and reacting the obtained compound, salt or solvate thereof with a compound of the formula (V):

$$R^3NH-Z \quad (V)$$

wherein $R^3$ is hydrogen or lower alkyl; Z is optionally substituted lower alkyl, optionally substituted lower alkenyl, optionally substituted amino, optionally substituted lower alkoxy, optionally substituted carbocyclyl or optionally substituted heterocyclyl,
salt or solvate thereof (hereinafter referred to as Compound (V)).
(8) A compound of the formula (IIIb-1):

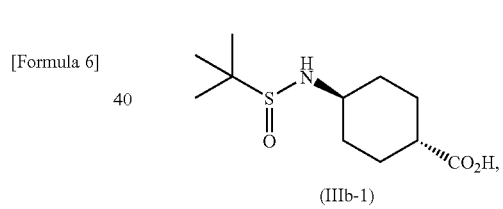

[Formula 10]

(IIIb-1)

salt or solvate thereof.

Effect of the Invention

A process for the preparation of the present invention can be used to obtain safely and easily Compound (III) or (IV) in high yield, and is useful for green chemistry.

BEST MODE FOR CARRYING OUT THE INVENTION

In this description, "lower alkyl" includes C1 to C10, preferably C1 to C6, and more preferably C1 to C3 straight or branched alkyl. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. "Lower alkyl" of $R^1$, $R^{1a}$ or $R^3$ is preferably methyl or ethyl. "Lower alkyl" of $R^2$ is preferably ethyl, isopropyl or t-butyl.

The lower alkyl part of "aryl lower alkyl", "halogeno lower alkyl" or "hydroxy lower alkyl" is the same as the above "lower alkyl".

Examples of substituents for "optionally substituted lower alkyl" of Z include (1) halogen; (2) cyano; and (3) the following groups (i) to (xvi): (i) hydroxy, (ii) lower alkoxy, (iii) mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkylcarbamoyl, (xiii) lower alkylthiocarbamoyl, (xiv) amino, (xv) lower alkylamino or (xvi) heterocyclylcarbonyl, which may be optionally substituted by at least one of groups selected from Substituent Group β defined below.

Examples of substituents for "optionally substituted lower alkyl" of $R^1$ or $R^{1a}$ include at least one of groups selected from the group consisting of halogen, optionally protected hydroxy, mercapto, lower alkoxy, lower alkenyl, di-lower alkylamino, lower alkylthio, acyl, carboxy, lower alkoxycarbonyl, carbamoyl, cyano, cycloalkyl phenoxyl and heterocyclyl.

Examples of substituents for "optionally substituted lower alkyl" except for those of Z, $R^1$ and $R^{1a}$ include at least one of groups selected from Substituent Group β defined below.

"Lower alkenyl" includes C2 to C10, preferably C2 to C8 and more preferably C3 to C6 straight or branched alkenyl having at least one double bond at arbitrary positions. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

Examples of substituents for "optionally substituted lower alkenyl" include halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl and/or heterocyclyl.

Examples of substituents for "optionally substituted amino" include the below Substituent Group β, optionally substituted benzoyl and/or optionally substituted heterocyclylcarbonyl (wherein the substituent is hydroxy, lower alkyl, lower alkoxy and/or lower alkylthio).

The lower alkyl part of "lower alkoxy", "lower alkylthio", "lower alkylcarbamoyl", "lower alkylthiocarbamoyl", "lower alkylamino", "di-lower alkylamino", "lower alkylsulfinyl", "lower alkylsulfonyl", "lower alkylsulfamoyl", "lower alkoxycarbonyl", "lower alkoxy lower alkyl", "hydroxy lower alkyl", "lower alkoxycarbonylamino", "lower alkylphenyl", "lower alkoxyphenyl", "halogeno lower alkyl", "phenyl lower alkoxy" or "phenyl lower alkylthio" is the same as the above "lower alkyl".

Examples of substituents for "optionally substituted lower alkoxy" include at least one of groups selected from the below Substituent Group β. Preferred is phenyl, lower alkylphenyl, lower alkoxyphenyl, naphthyl or heterocyclyl.

"Acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples include formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl.

The acyl part of "acyloxy" is the same as above.

The protecting group of "optionally protected hydroxy" or "optionally protected hydroxy lower alkyl" includes all hydroxy protecting groups usually used. Examples include acyl (e.g., acetyl, trichloroacetyl and benzoyl), lower alkoxycarbonyl (e.g., t-butoxycarbonyl), lower alkylsulfonyl (e.g., methanesulfonyl), lower alkoxy lower alkyl (e.g., methoxymethyl) and trialkylsilyl (e.g., t-butyldimethylsilyl).

"Halogen" includes fluorine, chlorine, bromine and iodine. Especially preferred is Fluorine or chlorine.

The halogen part of "halogenophenyl" or "halogeno lower alkyl" is the same as the above "halogen".

"Alkylenedioxy" includes methylenedioxy, ethylenedioxy, trimethylenedioxy, tetramethylenedioxy, pentamethylenedioxy and hexamethylenedioxy. Preferred is methylenedioxy or ethylenedioxy.

"Carbocyclyl" includes "cycloalkyl", "cycloalkenyl", "bicycloalkyl" and "aryl".

"Cycloalkyl" includes C3 to C8 and preferably C5 or C6 cyclic alkyl. Examples include cyclopropyl, cyclobutyl, cyclopentyl, cyclohexyl, cycloheptyl and cyclooctyl.

Examples of substituents for "optionally substituted cycloalkyl" include at least one of groups selected from Substituent Group β defined below.

"Cycloalkenyl" includes the above cycloalkyl with at least one of double bonds at arbitrary positions in the ring. Examples include cyclopropenyl, cyclobutenyl, cyclopentenyl, cyclohexenyl and cyclohexadienyl.

"Bicycloalkyl" includes C5 to C8 alicyclic groups wherein the two rings share two or more atoms and which are given by removing one hydrogen from C5 to C8 alicyclic group. Examples include bicyclo[2.1.0]pentyl, bicyclo[2.2.1]heptyl, bicyclo[2.2.2]octyl and bicyclo[3.2.1]octyl.

"Aryl" includes monocyclic or polycyclic aromatic carbocyclyl, and examples include phenyl, naphthyl, anthryl and phenanthryl. It also includes aryl which is fused with another non-aromatic carbocyclyl, and examples include indanyl, indenyl, biphenylyl, acenaphthyl, tetrahydronaphthyl and fluorenyl. Especially preferred is phenyl.

Examples of substituents for "optionally substituted carbocyclyl" include at least one of groups selected from the below Substituent Group α and β. The "carbocyclyl" may be substituted at arbitrary positions.

Examples of substituents for "optionally substituted aryl" or "optionally substituted aryl lower alkyl" of $R^1$ or $R^{1a}$ include at least one of groups selected from the group consisting of halogen, optionally protected hydroxy, mercapto, lower alkyl, halogeno lower alkyl, hydroxy lower alkyl, lower alkoxy, lower alkenyl, di-lower alkylamino, lower alkylthio, acyl, carboxy, lower alkoxycarbonyl, carbamoyl, cyano, cycloalkyl, phenyl, phenoxyl, lower alkyl phenyl, lower alkoxy phenyl, halogenophenyl, naphthyl and heterocyclyl.

Examples of substituents for the other "optionally substituted aryl" include at least one of groups selected from the below Substituent Group β.

The cycloalkyl part of "cycloalkylcarbamoyl", "cycloalkylsulfamoyl" or "cycloalkyloxy" is the same as the above "cycloalkyl".

The aryl part of "arylsulfonyl" or "aryl lower alkyl" is the same as the above "aryl".

"Heterocyclyl" includes heterocycle which contains at least one hetero atom optionally selected from the group of O, S and N. Examples include 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; fused bicyclic heterocyclyl such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, naphthyridinyl, dihydropyridyl, tetrahydroquinolyl and tetrahydrobenzothienyl; fused tricyclic heterocyclyl such as carbazolyl, acridinyl, xanthenyl, phenothiazinyl, phenoxathiinyl, phenoxazinyl and dibenzofuryl; non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

Fused heterocyclyl which is fused with a ring other than heterocycle (e.g., benzothiazolyl) may have a bonding radical on any ring.

Preferred as heterocyclyl of Z is imidazolyl, benzothiazolyl, isothiazolyl, benzopyranyl, morpholino, pyridyl, quinolyl, pyrimidyl or the like.

Examples of substituents for "optionally substituted heterocyclyl" are the same as the substituents for the above substituted "carbocyclyl".

The heterocyclyl part of "heterocyclyloxy", "heterocyclylthio", "heterocyclylcarbonyl" or "heterocyclylsulfonyl" is the same as the above "heterocyclyl".

Substituent Group α is a group of (1) halogen; (2) oxo; (3) cyano; (4) nitro; (5) imino optionally substituted by lower alkyl or hydroxy; (6) the following groups (i) to (xxi): (i) hydroxy, (ii) lower alkyl, (iii) lower alkenyl, (iv) lower alkoxy, (v) carboxy, (vi) lower alkoxycarbonyl, (vii) acyl, (viii) acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl, which may be optionally substituted by at least one of groups selected from Substituent Group β; (7) the following groups (i) to (v): (i) cycloalkyl, (ii) cycloalkenyl, (iii) cycloalkyloxy, (iv) amino and (v) alkylenedioxy, which may be optionally substituted by a substituent selected from Substituent Group β, lower alkyl, lower alkoxy-lower alkyl, optionally protected hydroxy-lower alkyl, halogeno-lower alkyl, lower alkylsulfonyl and/or arylsulfonyl; and (8) the following groups: (i) phenyl, (ii) naphtyl, (iii) phenoxy, (iv) phenyl-lower alkoxy, (v) phenylthio, (vi) phenyl-lower alkylthio, (vii) phenylazo, (viii) heterocyclyl, (ix) heterocyclyloxy, (x) heterocyclylthio, (xi) heterocyclylcarbonyl and (xii) heterocyclylsulfonyl, which may be optionally substituted by a substituent selected from Substituent β, lower alkyl, halogeno-lower alkyl and/or oxo.

Substituent Group β is a group of halogen, optionally protected hydroxy, mercapto, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, phenoxyl, lower alkylphenyl, lower alkoxyphenyl, halogenophenyl, naphthyl and heterocyclyl.

A compound of the formula (I), (III), (IV) or (VI) in the present invention may be the salt. Examples include salts of inorganic acid such as hydrochloric acid, sulfuric acid, nitric acid and phosphoric acid; salts of organic acid such as acetic acid, formic acid, p-toluenesulfonic acid, methanesulfonic acid, oxalic acid and citric acid; salts of organic base such as ammonium, trimethylammonium and triethylammonium; salts of alkali metal such as sodium and potassium; and salts of alkaline-earth metal such as calcium and magnesium.

Compound (III) or (IV) can be prepared according to the following processes.

Process A

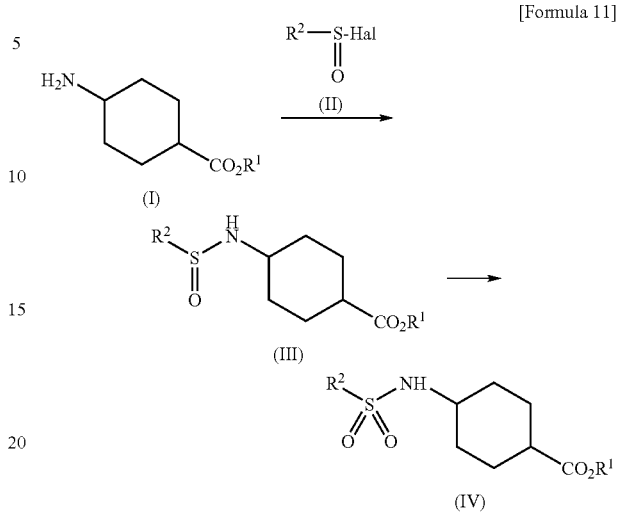

[Formula 11]

In the formula, $R^1$ is hydrogen, optionally substituted lower alkyl, optionally substituted aryl or optionally substituted aryl lower alkyl, $R^2$ is optionally substituted lower alkyl, optionally substituted cycloalkyl or optionally substituted aryl, and Hal is halogen.

(The First Step)

Compound (I) is reacted with sulfinylhalide Compound (II) in toluene solvent in the presence of at least one of additives selected from the group consisting of water, alcohol, dimethylformamide, dimethylacetamide and dimethoxyethane, if necessary, with base to give Compound (III).

The amount of Compound (II) can be about 1 mole equivalent or more and preferably about 1.3 mole equivalents or more, and about 3 mole equivalents or less and preferably about 1.5 mole equivalents or less relative to 1 mole of Compound (I).

Examples of additives include water, methanol, ethanol, isopropanol, n-propanol, n-butanol, t-butanol, dimethylformamide, dimethylacetamide, dimethoxyethane and the mixture of 2 or 3 kinds of additives selected from them. Preferred is water or isopropanol.

It is preferable that the amount of the additive is decided considering the amount of Compound (I) and (II), solubility, stability against the additive and the like. For example, when the weight of Compound (I) is v (g), the amount of the additive can be about 0.5 v (ml) or more and preferably about 1 v (ml) or more, and about 5 v (ml) or less and preferably about 2 v (ml) or less.

The amount of the toluene solvent is not especially limited. The arbitrary amount to give a reactive solution or slurry can be used. For example, when the weight of Compound (I) is v (g), the amount of the solvent can be about 1 v (ml) or more and preferably about 2 v (ml) or more. The maximum amount is not especially limited, but about 10 v (ml), preferably about 8 v (ml) and more preferably about 5 v (ml) considering preparation efficiency.

Examples of bases include triethylamine, pyridin, diisopropylethylamine, sodium hydroxide, potassium carbonate and sodium hydrogencarbonate. The amount of the base is about 1 mole equivalent or more and preferably about 2 mole equivalents or more, and about 5 mole equivalents or less and preferably about 4 mole equivalents or less relative to 1 mole of Compound (I).

Reaction can be carried out at −20° C. to under heating, preferably about −10 to 50° C. and more preferably about 0 to 20° C., for about 5 minutes to 10 hours and preferably about 1 to 3 hours.

The obtained Compound (III) may be isolated or provided to the next step without isolating. When it is used in the next step without isolating, there is an advantage that the works can be carried out in succession.

As a solvent used in this step, toluene is especially preferable, but acetic ester (ethyl acetate, methyl acetate, isopropyl acetate or isobutyl acetate), tetrahydrofuran, benzene, xylene, benzene chloride, dichloromethane or the like can be used.

(The Second Step)

Compound (IV) is obtained by subjecting Compound (III) to oxidation reaction in an appropriate solvent with an arbitrary oxidizing agent by a well-known method.

A solvent can be selected considering property of a substrate or an oxidizing agent or the like. Examples include toluene, dimethylformamide, tetrahydrofuran and ethyl acetate.

The reaction solution obtained in the first step without isolating Compound (III) can be subjected to oxidation reaction. In case that Compound (III) in the reaction solution obtained in the first step is a compound wherein $R^1$ is hydrogen, it is possible that Compound (III) is transformed to the salt, the water is added thereto and the mixture is subjected to oxidation reaction in an aqueous solution by a well-known method. Toluene same as previous step or water is preferably used as a solvent.

The amount of the solvent is not limited. The arbitrary amount to give a reactive solution or slurry can be used. For example, when the weight of Compound (III) is v (g), the minimum amount of the solvent is about 1 v (ml), preferably about 2 v (ml) and more preferably about 3 v (ml). The maximum amount is not limited, but about 10 v (ml), preferably about 8 v (ml) and more preferably about 5 v (ml) considering preparation efficiency.

An arbitrary oxidizing agent can be used. Examples of oxidizing agents include peracetic acid, m-chloroperbenzoic acid, pertrifluoroacetic acid, sodium periodate, magnesium monoperoxy phthalate (MMPP), potassium permanganate, sodium hypochlorite, calcium hypochlorite, perchloric acid, chlorous acid, oxone ($2KHSO_5 \cdot KHSO_4 \cdot K_2SO_4$) and $O_2$. Preferred is peroxide.

Peroxide can be used as hydrogen peroxide solution. As a catalyst, ammonium molybdate tetrahydrate (($NH_4)_6Mo_7O_{24} \cdot 4H_2O$), sodium tungstate, the hydrate or the like can be used. The amount of superoxide can be about 0.5 mole equivalent or more and preferably about 1 mole equivalent or more, and about 3 mole equivalents or less and preferably 2 mole equivalents or less relative to 1 mole of Compound (III). The minimum amount of catalyst can be about 0.005 mole equivalent or more and preferably about 0.01 mole equivalent or more, and about 0.1 mole equivalent or less and preferably about 0.06 mole equivalent or less relative to 1 mole of Compound (III).

Reaction temperature is not limited, but usually about 0 to 100° C. and preferably about 20 to 60° C.

Reaction time is not limited, but usually about 1 to 24 hours and preferably about 1 to 5 hours After finishing the reaction, the target compound, Compound (IV), is crystallized by adding acid such as sulfuric acid or hydrochloric acid at about 10 to 50° C. and preferably about 20 to 30° C., and stirring for about 15 minutes to 10 hours and preferably about 30 minutes to 3 hours. And then, the target compound, Compound (IV), can be obtained by washing, filtrating and drying by a well-known method.

As shown in a comparative example described below, when Compound (I) and (II) were reacted in the absence of an additive in toluene solvent, preparation rate of the target compound, Compound (III), remained around 50%. Furthermore, the present inventors confirmed that preparation rates of Compound (III) were changed by lot because the reactivity of Compound (I) changed by factors such as crystal form. On the other hand, a process of the present invention was preferably and stably carried out in all lots by reacting Compound (I) and (II) in the presence of an additive and the target compound, Compound (III), can be stably obtained with a high preparation rate, about 95%.

The present inventors confirmed that the solubility of Compound (I) in toluene was lower than that in ethyl acetate or tetrahydrofuran in Patent Document 2. In this circumstance, people skilled in the art should expect that it is usually difficult to carry out the reaction. However, according to a process of the present invention, the target compound could be obtained at very high preparation rate by using an additive. Additionally, although Compound (II) is unstable in water or the like, the reaction is preferably carried out without degradation of Compound (II) according to a process of the present invention.

Compared to processes described in Patent Document 1 or 2, the present process is useful as a process for the industrial preparation because the first step and the second step can be carried out in succession and the target compound can be obtained without dichloromethane or the like whose use is not environmentally preferable.

Process B

When Compound (III) obtained by the first step of the above Process A is a compound wherein $R^1$ is optionally substituted lower alkyl, optionally substituted aryl or optionally substituted aryl lower alkyl, Compound (IIIb) can be obtained by subjecting to the hydrolyzing step before the second step of the above Process A, and then subjected to oxidation reaction.

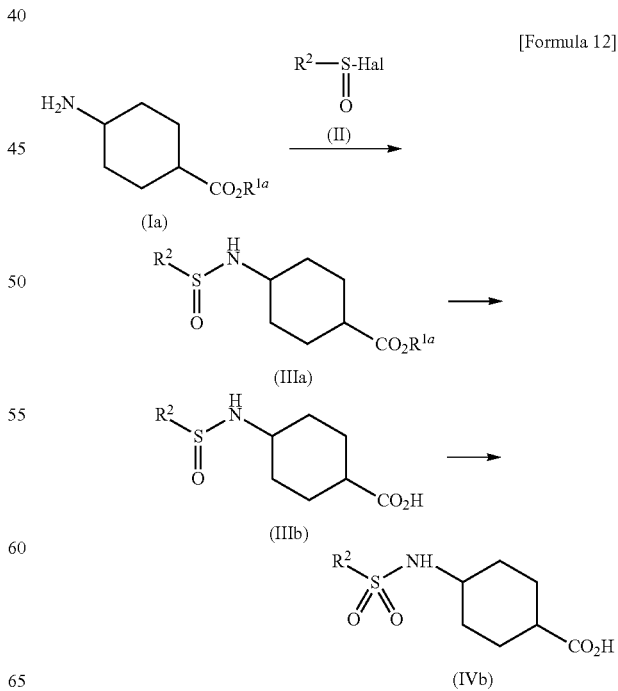

[Formula 12]

In the formula, $R^{1a}$ is optionally substituted lower alkyl, optionally substituted aryl or optionally substituted aryl lower alkyl, $R^2$ is optionally substituted lower alkyl, optionally substituted cycloalkyl or optionally substituted aryl, and Hal is halogen.

(The First Step)

Compound (IIIa) is obtained by the same process as the first step of the above Process A.

(The Second Step)

Compound (IIIb) is obtained by hydrolyzing Compound (IIIa) in an appropriate solvent with arbitrary base and water by a well-known method.

A solvent can be selected considering property of a substrate or oxidizing agent or the like. Examples include toluene, dimethylformamide, tetrahydrofuran, benzene, xylene, benzene chloride and dichloromethane.

The amount of solvent is not limited. The arbitrary amount to give a reactive solution or slurry can be used. For example, when the weight of Compound (IIIa) is v (g), the minimum amount of the solvent is about 1 v (ml), preferably about 2 v (ml) and more preferably about 3 v (ml). The maximum amount is not limited, but about 10 v (ml), preferably about 8 v (ml) and more preferably about 5 v (ml) considering preparation efficiency. Base and water are added to the prepared solution as above.

Alternatively, base and water can be added to a reaction solution without isolating Compound (IIIa) obtained by the first step.

The additive amount of water is not especially limited. For example, when the weight of Compound (IIIa) is v (g), the minimum amount of added water is about 1 v (ml), preferably about 2 v (ml) and more preferably about 3 v (ml). The maximum amount is not limited, but about 10 v (ml), preferably about 8 v (ml) and more preferably about 5 v (ml) considering preparation efficiency. When Compound (IIIa) obtained in the first step is subjected to this step as a reaction solution without isolating, the minimum amount of added water is about half of and preferably about the same as the volume of the reaction solution. The maximum amount is about 10 times and preferably about 3 times of the volume of the reaction solution.

As a base, sodium hydroxide, sodium methoxide, potassium hydroxide or the like can be used. The amount of the base can be about 1 mole equivalent or more and preferably about 2 mole equivalents or more, and about 5 mole equivalents or less and preferably about 3 mole equivalents or less relative to 1 mole of Compound (IIIa).

Reaction temperature is not limited, but usually about 0 to 80° C. and preferably about 20 to 50° C.

Reaction time is preferably about 1 to 24 hours and more preferably about 1 to 10 hours.

Compound (IIIb) may be isolated from the water layer of the obtained reaction solution or provided to the next step as water layer without isolating. When it is used in the next step without isolating, there is an advantage that the works can be carried out in succession.

When peroxide is used as an oxidizing agent in the next step, oxidation reaction can be preferably carried out by neutralizing the reaction solution with acid such as sulfuric acid and hydrochloric acid in advance.

(The Third Step)

The target compound, Compound (IVb), is obtained by the same process as the second step of the above Process A.

Patent Document 2 described above discloses a method for coupling Compound (I) and (II) to give Compound (IIIa), oxidizing Compound (IIIa) to give Compound (IV) wherein $R^1$ is lower alkyl, and hydrolyzing after transforming Compound (IV) to trans isomer to give Compound (IVb). According to this method, the yield from Compound (Ia) to Compound (IVb) was around 50%. The yield remained only 70% or less even if the loss in the transformation step to trans isomer was excluded. Furthermore, the reaction was carried out by isolating each reaction intermediate and changing the reaction solvent to a different solvent such as ethyl acetate, dimethylformamide, toluene or tetrahydrofuran.

The present inventors found that Compound (IIIa) was degraded under the acid condition, and completed a method for obtaining the target compound, Compound (IVb), with high yield, around 90% (yield from Compound (I)), by subjecting to oxidation reaction after alkaline hydrolysis. According to a process of the present invention, the target compound can be efficiently and safely obtained because steps from the first step to the third step can be carried out in succession and dichloromethane or the like is not used.

Compound (VI) can be prepared by reacting Compound (IVb) obtained in the above Process A or B with Compound (V).

When a compound wherein $R^1$ is optionally substituted lower alkyl, optionally substituted aryl or optionally substituted aryl lower alkyl, salt or solvate thereof (hereinafter referred to as Compound (IVa)) can be obtained by the above Process A, the compound is transformed to Compound (IVb) by hydrolyzing in advance.

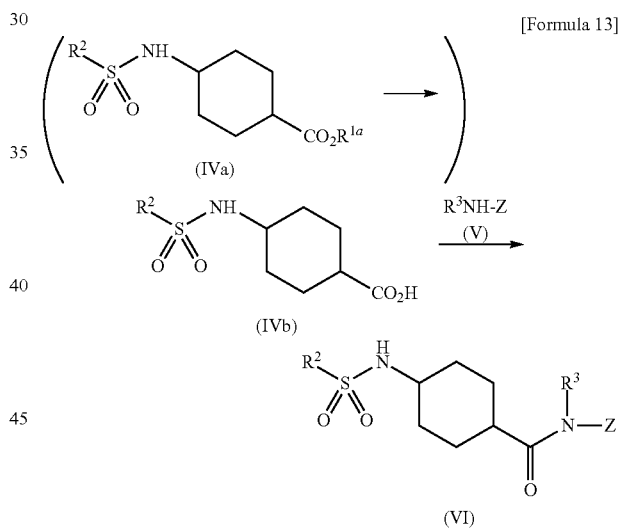

[Formula 13]

In the formula, $R^{1a}$ is optionally substituted lower alkyl, optionally substituted aryl or optionally substituted aryl lower alkyl, $R^2$ is optionally substituted lower alkyl, optionally substituted cycloalkyl or optionally substituted aryl, $R^3$ is hydrogen or lower alkyl, and Z is optionally substituted lower alkyl, optionally substituted lower alkenyl, optionally substituted amino, optionally substituted lower alkoxy, optionally substituted carbocyclyl or optionally substituted heterocyclyl.

Compound (VI) can be obtained by reacting Compound (V) with Compound (IVb). This reaction can be carried out according to amidation reaction described in the above Patent Document 1 or the like.

For example, Compound (IVb) and an activator such as acid halide (for example, thionyl chloride, oxalyl chloride, phosphorus oxychloride or the like is used), acid anhydride or activated ester of Compound (V) are reacted in an appropriate solvent at about 0 to 100° C. for about 3 minutes to 10 hours.

As a solvent, tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, the mixture solvent or the like can be used. Preferred is toluene or tetrahydrofuran. Additionally, if necessary, activator such as base (Preferred is triethylamine, pyridine or the like), thionyl chloride, acid halide (e.g., thionyl chloride, oxalyl chloride or phosphorus oxychloride), acid anhydride or activated ester can be used.

As the alternative process, the target compound can be obtained by reacting Compound (IVb) and (V) in an appropriate solvent (e.g., tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water or the mixture solvent) in the presence of a condensing agent at about 0 to 100° C. for about 3 minutes to 10 hours.

Examples of condensing agents include 1,1-carbonyldiimidazole, dicyclohexyl carbodiimide and water soluble carbodiimide (1-ethyl-3-(3'-dimethylamino propyl)carbodiimide).

Examples of the groups of Z are the followings.

[Formula 14]

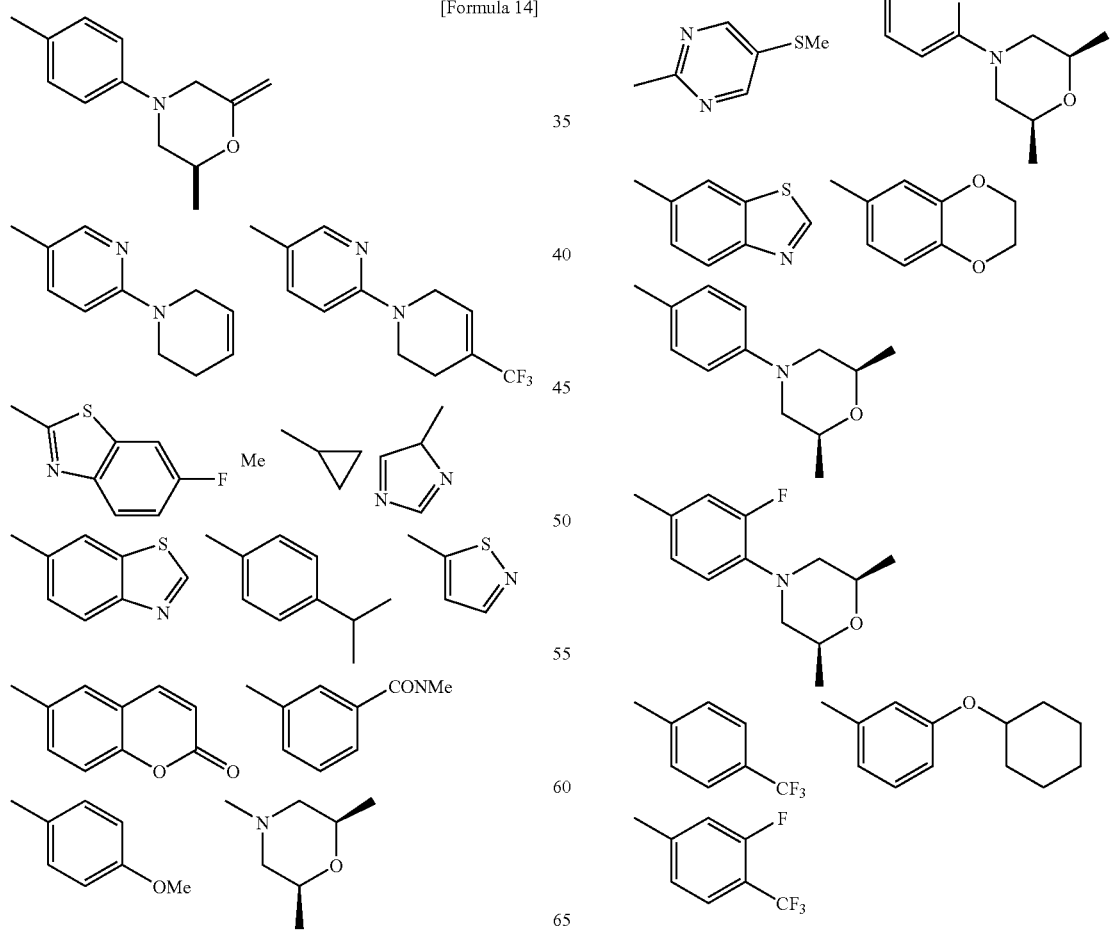
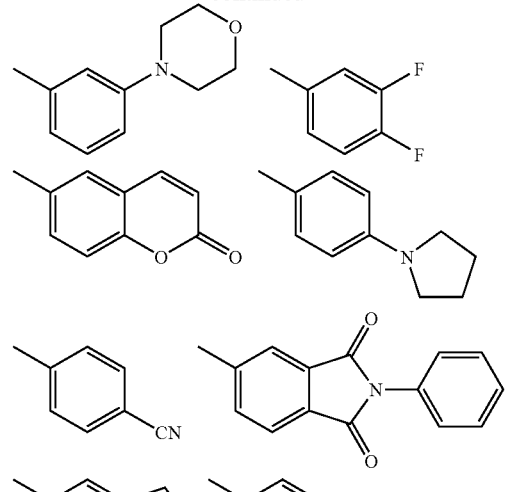
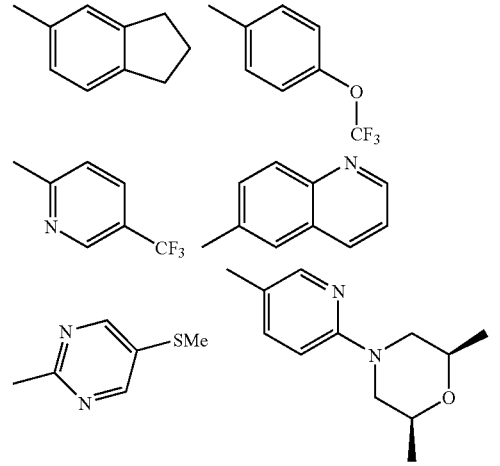
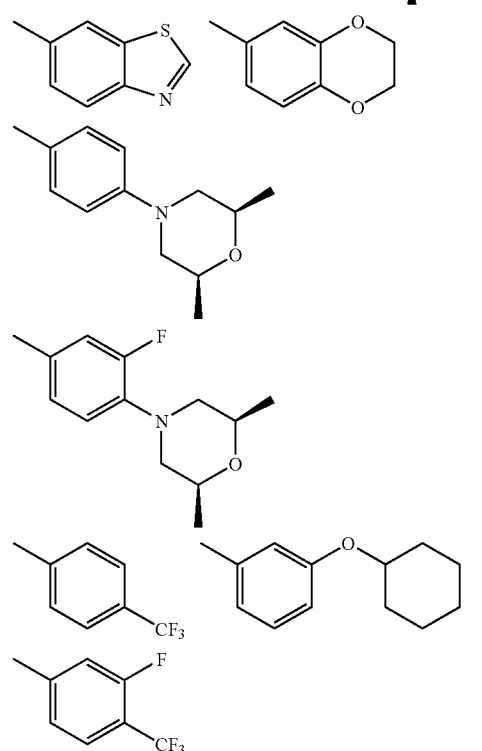

Compound (VI) obtained as above is useful as a NPYY5 receptor antagonist.

This invention is further explained by the following Examples, which are not intended to limit the scope of the present invention.

Example 1

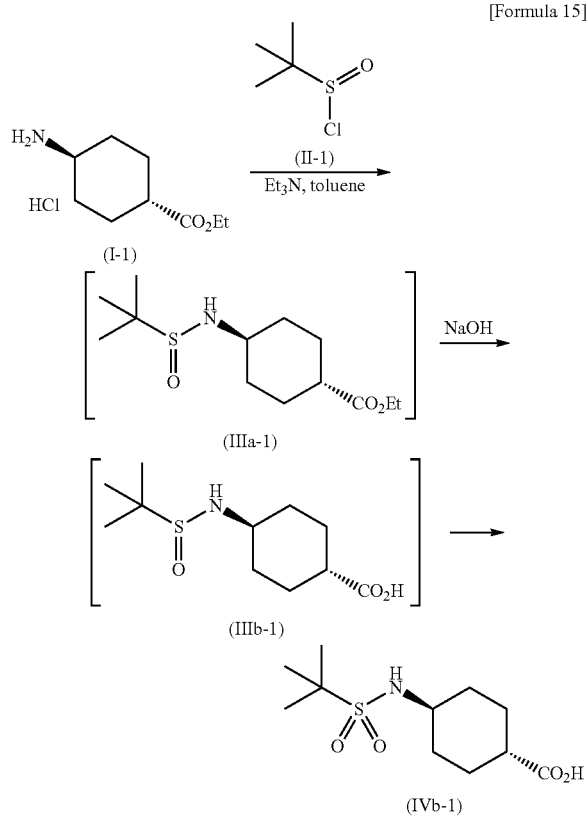

[Formula 15]

Additive: Water

To hydrochloride of Compound (I-1) (10.00 g), were added toluene (40 mL), triethylamine (10.72 g) and tap water (20 mL) and the mixture was cooled to 3° C. Compound (II-1) (7.45 g) was added dropwise thereto at 3 to 6° C. over 65 minutes. This reaction solution was stirred at 0 to 10° C. for about 60 minutes and then separated to obtain the upper layer (46.69 g) (Compound (IIIa-1) in toluene solution). To this reaction solution, were added tap water (40 mL) and 48% NaOH solution (10.03 g). The mixture was stirred at about 40° C. for 2 hours, and then separated to obtain the lower layer. 20% sulsuluric acid solution (17.54 g) was added dropwise thereto at 40 to 48° C. to be pH6.5 (Compound (IIIb-1) in the reaction solution). To this reaction solution, was added sodium tungstate dihydrate (794 mg). 35% hydrogen peroxide solution (9.36 g) was added dropwise thereto at 32 to 52° C. over 61 minutes. This reaction solution was stirred at about 40° C. for 90 minutes. 18.12 g of a solution that sodium sulfite (8.00 g) was dissolved in tap water (100 g) was added dropwise thereto and the surplus superoxide was removed. To this reaction solution, was added dropwise 20% sulsuluric acid solution (12.32 g) at 40 to 45° C. to be pH3. The mixture was stirred at about 2° C. for 120 minutes. The reaction mixture was filtered, and then the filtrate was washed with 30 mL of tap water. The undried crystal was collected and dried under reduced pressure with heating (80° C.) to give 11.41 g of Compound (IVb-1) (90.0% yield, based on hydrochloride of Compound (I-1)).

Compound (IIIb-1)

$^1$H-NMR (CDCl$_3$, internal standard TMS, 300 MHz) δ 1.05-1.20 (m, 2H), 1.21 (s, 9H), 1.54 (m, 2H), 2.09 (t, 4H, J=14 Hz), 2.28 (tt, 1H, J=12.0, 3.6 Hz), 3.18 (m, 1H), 3.30 (d, 1H, J=6.0 Hz)

Elemental Analysis:
Calcd: C, 53.41; H, 8.56; N, 5.66; S, 12.96.
Found: C, 53.21; H, 8.59; N, 5.85; S, 12.57.
Melting point: Degrading over about 180° C.

Example 2

Additive: Isopropanol

To hydrochloride of Compound (I-1) (7.00 g), were added toluene (28 mL), triethylamine (7.50 g) and isopropanol (7 mL) and the mixture was cooled to 3° C. Compound (II-1) (5.21 g) was added dropwise thereto at 2 to 8° C. over 17 minutes. This reaction solution was stirred at 0 to 10° C. for about 60 minutes. Tap water (14 mL) was added thereto and separated to obtain the upper layer (36.31 g) (Compound (IIIa-1) in toluene solution). To this reaction solution, were added tap water (28 mL) and 48% NaOH solution (7.02 g). The mixture was stirred at about 25° C. for 4 hours, and then separated to obtain the lower layer. 20% sulsuluric acid solution (12.73 g) was added dropwise thereto at about room temperature to be pH7.5 (Compound (IIIb-1) in the reaction solution). To this reaction solution, was added sodium tungstate dihydrate (556 mg). 35% hydrogen peroxide solution (6.55 g) was added dropwise thereto at 40 to 43° C. over 59 minutes. After stirring this reaction solution at about 40° C. for 120 minutes, 4.63 g of a solution that sodium sulfite (8.00 g) was dissolved in tap water (100 g) was added dropwise thereto and the surplus superoxide was quenched. To this reaction solution, was added dropwise 20% sulsuluric acid solution (8.39 g) at about room temperature to be pH3. The mixture was stirred at about 2° C. for about 30 minutes. The reaction mixture was filtered, and then the filtrate was washed with 21 mL of tap water. The undried crystal was collected and dried under reduced pressure with heating (80° C.) to give 7.86 g of Compound (IVb-1) (88.5% yield, based on hydrochloride of Compound (I-1)).

Example 3

Additive: Methanol

To hydrochloride of Compound (I-1) (7.00 g), were added toluene (35 mL), triethylamine (7.50 g) and methanol (7 mL) and the mixture was cooled to 3° C. Compound (II-1) (5.21 g) was added dropwise thereto at 2 to 9° C. over 48 minutes. Triethylamine (7.50 g) was added thereto and Compound (II-1) (5.21 g) was added dropwise at 2 to 9° C. Triethylamine (7.50 g) was added thereto and Compound (II-1) (5.21 g) was added dropwise at 2 to 9° C. After stirring this reaction solution at 0 to 10° C. for about 30 minutes, tap water (14 mL) was added thereto and separated to obtain the upper layer (46.57 g) (Compound (IIIa-1) in toluene solution). The preparation rate of Compound (IIIa-1) was 94.5%.

The preparation rates of Compound (IIIa-1) in the above Examples and a case that the additive was not added were compared.

TABLE 1

| | Additive | The amount of the additive | The kind and amount of the solvent | The preparation rate (%) of Compound (IIIa-1) |
|---|---|---|---|---|
| Example 1 | Water | 2V | Toluene 4V | 94.6 |
| Example 2 | Isopropanol | 1V | Toluene 4V | 98.8 |
| Example 3 | Methanol | 1V | Toluene 5V | 94.5 |
| Comparative example | No additive | — | Toluene 5V | 52.7 |

(1V of the amount of an additive means 1 mL relative to 1 g of the substrate.)

To carry out the next reaction without isolating Compound (IIIa-1), the preparation rate was calculated by quantitating the reaction solution with HPLC without isolating the compound in all cases.

It is cleared that the preparation rates of Compound (IIIa-1) were considerably enhanced in the cases that an additive was added compared to the case that an additive was not used.

INDUSTRIAL APPLICABILITY

A process of the present invention is useful as a process for the industrial preparation because it can safely and efficiently prepare Compound (III) and (IV).

The invention claimed is:

1. A process for the preparation of a compound of the formula (III):

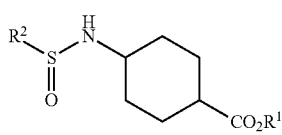
(III)

wherein $R^1$ is hydrogen or optionally substituted lower alkyl, and $R^2$ is lower alkyl, or a salt thereof,
comprising reacting a compound of the formula (I):

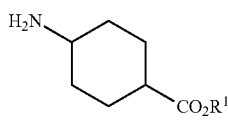
(I)

wherein $R^1$ is hydrogen or optionally substituted lower alkyl,
or a salt thereof with a compound of the formula (II):

(II)

wherein $R^2$ is lower alkyl, and Hal is halogen,
in toluene solvent in the presence of water or alcohol.

2. The process of claim 1, wherein the additive is water or isopropanol.

3. A process for the preparation of a compound of the formula (IV):

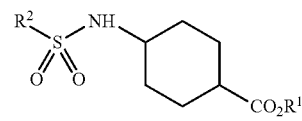
(IV)

wherein $R^1$ is hydrogen or optionally substituted lower alkyl and $R^2$ is lower alkyl,
or a salt thereof,
comprising obtaining a compound of the formula (III), or a salt thereof by the process of claim 1, and oxidizing the obtained compound or salt thereof.

4. A process for the preparation of a compound of the formula (IVb):

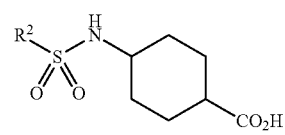
(IVb)

wherein $R^2$ is lower alkyl,
comprising obtaining a compound of the formula (IIIa):

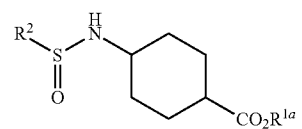
(IIIa)

wherein $R^{1a}$ is optionally substituted lower alkyl and $R^2$ is lower alkyl,
or a salt thereof, by the process of claim 1; hydrolyzing the compound of the formula (IIIa) under alkaline condition to obtain a compound of the formula (IIIb):

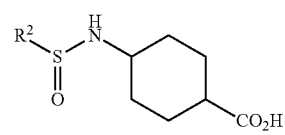
(IIIb)

wherein $R^2$ is lower alkyl; and
oxidizing the obtained compound.

5. The process for the preparation of a compound of the formula (IVb) as in claim 4, comprising reacting without isolating a compound of the formula (IIIa) or (IIIb) or the salt to give a compound of the formula (IVb), or a salt thereof.

* * * * *